United States Patent [19]

Reid

[11] Patent Number: 5,003,063
[45] Date of Patent: Mar. 26, 1991

[54] CONVERSION OF STEROIDAL 17-CYANOHYDRINS TO CORTICOIDS

[75] Inventor: John G. Reid, Kalamazoo, Mich.

[73] Assignee: The Upjohn Company, Kalamazoo, Mich.

[21] Appl. No.: 459,741

[22] PCT Filed: Jul. 22, 1988

[86] PCT No.: PCT/US88/02429
§ 371 Date: Jan. 30, 1990
§ 102(e) Date: Jan. 30, 1990

[87] PCT Pub. No.: WO89/01483
PCT Pub. Date: Feb. 23, 1989

[51] Int. Cl.$^5$ .................. C07J 3/00; C07J 5/00; C07J 19/00; C07J 75/00
[52] U.S. Cl. .................. 540/33; 540/36; 540/97; 540/27; 552/505; 552/521; 552/596
[58] Field of Search .................. 260/397.45, 397.47; 544/154, 403, 34, 35, 38, 88, 89, 99; 548/341, 574; 540/33, 36, 87, 97; 552/521, 505, 596

[56] References Cited

U.S. PATENT DOCUMENTS 4,424,159 1/1984 Biollaz .................. 260/397.45
4,548,748 10/1985 Van Rheenen .................. 260/397.45

FOREIGN PATENT DOCUMENTS 5758 5/1979 European Pat. Off. .
153001 8/1985 European Pat. Off. .
1369314 8/1964 France .
1369325 8/1964 France .
89348 10/1958 Netherlands .

OTHER PUBLICATIONS von Manfred Schlosser et al., "179.a-Hydroxymethylen-Verlangerte Aldehyde durch Schonende Reduktion von Cyanhydrinen", 1978, Helvetica Chimca Acta-vol. 61:1903-1911.
Corey, E. J. et al., "Total Synthesis of (+)-Aphidicolin", 1980, Journal Amer. Chemical Society 102.5:1742-1744.
Sandops et al., J. Org. Chem., 1978, 43(2)324-330, Chemical Abstracts, vol. 88, 1978, Abstract 62267t.
Agami et al., Tetrahedron, 1980, 36(20-21), 2977-2981, Chemical Abstracts, vol. 94, 1981, Abs. 138907y.
Tsitsa et al., Steroids, 1979, 33(1) 23-31, Chemical Abstracts, vol. 90, 1979, Abstract 204343g.
Djerassi, Steroid Reactions (1963 Holden-Day, San Francisco, 1983), pp. 3 and 49 to 50.
Freerksen, J. Org. Chem. 44(5), 1979, pp. 702-710.
Taguchi et al., JACS 96(9), May 1974, pp. 3010-3011.

Primary Examiner—Mukund J. Shah
Assistant Examiner—E. C. Ward
Attorney, Agent, or Firm—Bruce Stein

[57] ABSTRACT

The invention involves a two step chemical transformation of a steroidal 17-cyanohydrin (II)

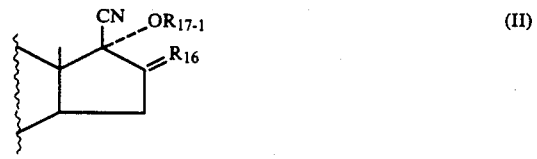

to a 17α-hydroxy-21-halo-20-keto steroid (IV)

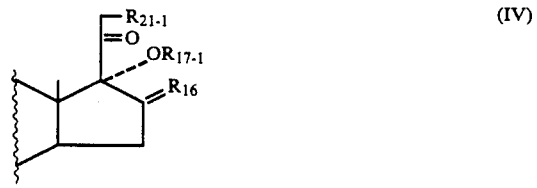

intermediate which can readily be converted to pharmaceutically useful corticoids.

16 Claims, No Drawings

CONVERSION OF STEROIDAL 17-CYANOHYDRINS TO CORTICOIDS

BACKGROUND OF THE INVENTION

1. Field of the Invention

The invention involves the chemical transformation of a steroidal 17-cyanohydrin to a 17α-hydroxy-21-halo-20-keto steroid intermediate which can readily be converted to pharmaceutically useful corticoids.

2. Description of the Related Art

17α-Hydroxy-17β-cyanosteroids (I) are known to those skilled in the art. The transformation of the 17α-hydroxy-17β-cyanosteroids (I) to 17α-hydroxyprotected-17β-cyanosteroids (II) is also known to those skilled in the art.

The reduction of nitriles to imines followed by hydrolysis to give aldehydes is well known in organic chemistry. U.S. Pat. No. 4,424,159 discloses the transformation of a $C_{17}$-cyano steroid to the corresponding steroidal $C_{17}$-carboxaldehyde using diisobutylaluminum hydride. However, because the other substituent at $C_{17}$ was —H, that reaction was much simpler and did not in any way indicate that the reduction of a compound of the formula STEROID-17α-[-O-protected]17β-[CN] would be operable. The transformation of ketone-derived, protected cyanohydrins to the corresponding protected aldehydes with sodium bis(2-methoxyethoxy)aluminum hydride in 57–70% yields is reported in Helv. Chim. Acta 61, 1903 (1978), see p. 1905. J.A.C.S. 102, 1742 (1980) reports the reduction of a trimethylsilyl protected cyanohydrin to the corresponding aldehyde in only 75% yield using 4 equivalents of diisobutylaluminum hydride in toluene at 0°. The transformation of protected steroidal cyanohydrins (II) to the corresponding protected steroidal aldehydes (III) has not been reported. The reduction of the 17α-hydroxy protected-17β-cyanosteroids (II) of the present invention surprisingly gives the protected aldehyde (III) in >90% yield.

Protected steroid aldehydes (III) are not known. Unprotected steroidal 17α-hydroxy-17β-carboxaldehydes are known, see French patents 1,369,325 ($A^{9(11)}$) and 1,369,314 (11-keto). Dutch patent 89,348 (11-keto) and Endocrinol. Japan 4, 214 (1957) (11β-hydroxy).

The conversion of a ketone to α-chloroketones via the addition of $Cl_2CHLi$ followed by treatment with butyllithium was reported in J. Organometal. Chem., 40, Cl (1972). The yield was only about 60% and the product was contaminated with 8–15% of α-chloroaldehydes formed in a competing rearrangement. The same reaction was reported, Tetrahedron Letters 4117 (1972), using lithium piperidide in place of butyllithium giving yields of 56, 70 and 87% using simple monofunctional ketones, not aldehydes. The authors did not take into account the yield for the formation of their substrate from aldehydes and ketones. The conversion of a simple monofunctional aldehyde to an α-bromoketone in 62% yield using $Br_2CHLi$ was reported in Bull. Soc. Chim. France 1797 (1975). The same authors then reported, J. Organometal. Chem., 97, 325 (1975), the conversion of a few more simple carbonyls to α-haloketones using $CH_2X_2$ and lithium piperidide. Yields of the reaction of the carbonyl with $X_2CHLi$ ranged from 50–87% (typically 60–65%) for production of the halohydrin and conversion of these adducts to α-haloketones in 60–90% yield (typically 70–80%) which gives a typical overall yield of about 40–60%. Many of these products contained 8–65% α-haloaldehyde, although some reactions provided the α-haloketone selectively. All of these references disclose reactions which involved the generation of $X_2CHLi$ where X is a bromine or chlorine atom by treating $X_2CH_2$ with either a lithium amide base or butyllithium at $<-70°$. Solutions of these reagents are unstable at temperatures above $-70°$. The process of the present invention avoids the need to work with such unstable solutions at such low temperatures.

J. Am. Chem. Soc., 96, 3010 (1974) and Bull. Chem. Soc. Japan 50, 1588 (1977) report a simple procedure for the reaction of methylene bromide with aldehydes and ketones to give the same halohydrin intermediates as described in the above references. Their procedure required the use of a large excess (2–24 equivalents) of $CX_2H_2$ and the yield with the aldehyde substrates was only 73–79%. The process of the present invention uses <3 equivalents of base, preferably about 2.8 equivalents, to transform the protected steroidal aldehyde (III) all the way to the desired protected 21-halo-17α-hydroxy-20-keto steroid (IV), not just to the halohydrin intermediate as with the above references.

The conversion of protected 21-halo-17α-hydroxy-20-keto steroids to the corresponding protected 21-acyloxy-17α-hydroxy-20-keto steroids and then to corticoids is well known to those skilled in the art.

SUMMARY OF INVENTION

Disclosed is a process for the preparation of a protected aldehyde of formula (III)

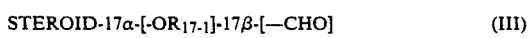

STEROID-17α-[-OR$_{17-1}$]-17β-[—CHO]          (III)

where $R_{17-1}$ is —Si—$(R_{17-2})_2(R_{17-3})$ where $R_{17-2}$ and $R_{17-3}$ are $C_1$–$C_4$ alkyl or φ, which comprises (1) contacting a protected cyanohydrin of formula (II)

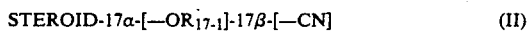

STEROID-17α-[—OR$_{17-1}$]-17β-[—CN]          (II)

where $R_{17-1}$ is as defined above with at least one hydride equivalent of a reducing agent in the presence of an ether and (2) hydrolyzing the reaction mixture of step (1).

Also disclosed is a process for the preparation of a protected 21-halo steroid of formula (IV)

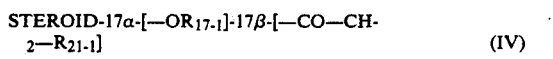

STEROID-17α-[—OR$_{17-1}$]-17β-[—CO—CH$_2$—R$_{21-1}$]          (IV)

where $R_{17-1}$ is —Si—$(R_{17-2})_2(R_{17-3})$ where $R_{17-2}$ and $R_{17-3}$ are $C_1$–$C_4$ alkyl or φ and $R_{21-1}$ is —Cl or —Br, which comprises (1) contacting a protected aldehyde of formula (III)

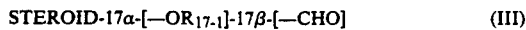

STEROID-17α-[—OR$_{17-1}$]-17β-[—CHO]          (III)

where $R_{17-1}$ is as defined above, with a strong base in the presence of a compound of the formula $CH_2(R_{21-1})_2$ where $R_{21-1}$ is as defined above.

Further disclosed is a protected aldehyde of formula (III)

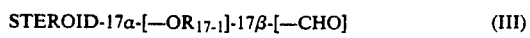

STEROID-17α-[—OR$_{17-1}$]-17β-[—CHO]          (III)

where $R_{17-1}$ is —Si—$(R_{17-2})_2(R_{17-3})$ where $R_{17-2}$ and $R_{17-3}$ are $C_1$–$C_4$ alkyl or φ.

Additionally disclosed is a process for the preparation of a protected 21-halo steroid of formula (IV)

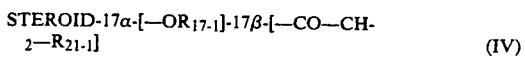

where $R_{17\text{-}1}$ is $-Si-(R_{17\text{-}2})_2(R_{17\text{-}3})$ where $R_{17\text{-}2}$ and $R_{17\text{-}3}$ are $C_1$-$C_4$ alkyl or $\phi$ and $R_{21\text{-}1}$ is $-CL$ or $-Br$, which comprises (1) contacting a protected cyanohydrin of formula (II)

STEROID-17α-[—OR$_{17\text{-}1}$]-17β-[—CN]   (II)

where $R_{17\text{-}1}$ is as defined above with at least one hydride equivalent of a reducing agent in the presence of an ether to produce a protected aldehyde of formula (III)

STEROID-17α-[—OR$_{17\text{-}1}$]-17β-[—CHO]   (III)

where $R_{17\text{-}1}$ is as defined above and (2) contacting the protected aldehyde of formula (III) with a strong base in the presence of a compound of the formula $CH_2(R_{21\text{-}1})_2$ where $R_{21\text{-}1}$ is as defined above.

DETAILED DESCRIPTION OF THE INVENTION

The steroidal cyanohydrins (I) are known to those skilled in the art or can be readily be prepared by methods known to those skilled in the art from known steroid starting materials. The steroid A-, B- and C- rings are known to those skilled in the art include the usual steroidal nucleus. More particularly, they include the A-, B- and C- rings set forth in CHART B.

First, the A-ring $C_3$ ketone of the cyanohydrins (I) is protected as is known to those skilled in the art, for example, as the alkyl $\Delta^{3,5}$-dienolether, $\Delta^5$-3-ketal or enamine. Next, the 17α-hydroxy group of the cyanohydrin is protected as is known to those skilled in the art. Suitable protecting groups include silyl ethers, acetals, or readily removed ethers. The silyl ether is the preferred protecting group but any group which remains on and protects the 17α-hydroxyl group during the reaction and is readily removable at the end of the process is acceptable. Preferred is the trimethylsilyl ether.

The protected cyanohydrin (II) is transformed to the corresponding protected aldehyde (III) by reaction with at least one hydride equivalent of a reducing agent. Suitable reducing agents are aluminum hydrides. These include diisobutylaluminum hydride, lithium aluminum hydride, sodium bis-(2-methoxyethoxy)aluminum hydride and lithium tri-tertbutoxyaluminum hydride. Preferred is diisobutylaluminum hydride. At least 1 hydride equivalent of reducing agent is necessary. Preferred is 1.2-2.0 equivalents, more preferred is 1.4-1.5 equivalents. The term "hydride equivalent" is used since one molar equivalent of some of the above reducing agents contain more than one hydride equivalent. The reaction is performed in any organic solvent compatible with the reducing agent, however some ether must be present. The quantity of ether may range from about 0.1% to 100%. Ethers include THF, ether and methyl t-butyl ether and mixtures thereof. Suitable co-solvents include the above ethers and toluene, methylene chloride and mixtures thereof. It is preferred that at least 0.1% ether be present, more preferably at least 0.5%, still more preferably at least 5% ether. The amount of ether depends on the particular ether, the particular reducing agent, the particular protected cyanohydrin (II) etc.

Preferred is methyl t-butyl ether containing about 10% THF (v/v). Temperature is not critical and the process can be performed from about $-80°$ to about 80°, preferably about $-30°$ to about 0°. Any order of addition is operable, the reducing agent can be added to the steroid or the steroid to the reducing agent. Following contacting the protected cyanohydrin (II) with at least one hydride equivalent of the reducing agent in the presence of an ether, the reaction mixture is hydrolyzed. It is preferred to perform the hydrolysis with aqueous acid. It is preferred that the acid be a carboxylic acid, it is preferred that the carboxylic acid be acetic acid.

The protected aldehyde (III) can be isolated by means known to those skilled in the art or can be carried on through to the next step without isolation; it is preferred that the protected aldehyde (III) be carried on without isolation. For the protected aldehyde (III) it is preferred that $R_{17\text{-}1}$ is trimethylsilyl. It is preferred that the protected aldehyde (III) A-ring have (A-I) $R_5$ is $R_{5\text{-}1}$:$R_{5\text{-}2}$, $R_6$ is $R_{6\text{-}1}$:$R_{6\text{-}2}$, $R_{10}$ is α-$R_{10\text{-}1}$:β-$R_{10\text{-}2}$ where one of $R_{6\text{-}1}$ and $R_{6\text{-}2}$ is $-H$ and the other taken together with one of $R_{5\text{-}1}$ and $R_{5\text{-}2}$ forms a second bond between $C_5$ and $C_6$, $R_{10\text{-}2}$ is $-CH_3$, $R_{10\text{-}1}$ and the other of $R_{5\text{-}1}$ and $R_{5\text{-}2}$ taken together are $-CH_2-CH_2-C)R_{3\text{-}1})=CH-$ where $R_{3\text{-}1}$ is $C_1$-$C_6$ alkyloxy, $-O-\phi$ where $\phi$ is optionally substituted with 1 $C_1$-$C_4$ alkyl;

(A-II) $R_5$ is $R_{5\text{-}3}$:$R_{5\text{-}4}$, $R_6$ is $R_{6\text{-}3}$:$R_{6\text{-}4}$, and $R_{10}$ is α-$R_{10\text{-}3}$:β-$R_{10\text{-}4}$, where one of $R_{6\text{-}3}$ and $R_{6\text{-}4}$ is $-H$ and the other taken together with one of $R_{5\text{-}3}$ and $R_{5\text{-}4}$ forms a second bond between $C_5$ and $C_6$, $R_{10\text{-}4}$ is $-CH_3$, $R_{10\text{-}3}$ and the other of $R_{5\text{-}3}$ and $R_{5\text{-}4}$ taken together are $-CH_2-CH_2-C(\alpha\text{-}R_{3\text{-}3})(\beta\text{-}R_{3\text{-}4})-CH_2-$, where $R_{3\text{-}3}$ and $R_{3\text{-}4}$ taken together are $-O-CH_2-C(CH_3)_2-CH_2-O-$ or $-O-(CH_2)_{n1}-O-$ where $n_1$ is 2 or 3. It is preferred that the protected aldehyde (III) C-ring have $R_{11}$ is $R_{11\text{-}1}$:$R_{11\text{-}2}$ or α-$R_{11\text{-}3}$:β-$R_{11\text{-}3}$ where $R_{11\text{-}3}$ and $R_{11\text{-}4}$ are both $-H$. It is preferred that the protected aldehyde (III) D-ring have $R_{16\text{-}1}$ and $R_{16\text{-}2}$ are both $-H$. The preferred protected aldehydes (III) are selected from the group consisting of 3,17α-dihydroxyandrosta-3,5,9(II)-triene-17β-carboxaldehyde 3-methyl 17-trimethylsilyloxy diether, 3,3,17α-trihydroxyandrost-5-ene-17β-carboxaldehyde 3,3-ethylene ketal 17-trimethylsilyloxy ether, 3,3,17α-trihydroxyandrosta-5,9(II)-diene-17β-carboxyaldehyde 3,3-ethylene ketal 17-trimethylsilyloxy ether.

The protected aldehyde (III) is transformed to the corresponding protected 21-halo steroid (IV) by contacting with a strong base in the presence of $CH_2(R_{21\text{-}1})_2$ where $R_{21\text{-}1}$ is $-Br$ or $-Cl$. Strong bases are amide bases of the formula Metal-N-$(R_1)_2$ where Metal is lithium, sodium, potassium and magnesium and $R_1$ is $-H$, $C_1$-$C_6$ alkyl, $-Si(R_2)_3$ where $R_2$ is $C_1$-$C_6$ alkyl. It is preferred that the amide is selected from the group consisting of lithium diisopropylamide, lithium diethylamide, lithium piperidide and lithium dicyclohexylamide. The preferred base is lithium diisopropylamide. It is preferred that the halogenated agent be methylene bromide. About 2.5 to 3, preferably 2.8, equivalents of strong base are utilized. One equivalent per equivalent of $CH_2R_{21}$ is needed plus 1.8 equivalents for the transformation of the halohydrin intermediate to the 21-halo ketone. Slightly greater than 1 equivalent of halogenated agent is required, preferably 1.05 equivalents. The reaction is performed in an etheral solvent with or without a hydrocarbon co-solvent. Preferred is about 50% hydrocarbon with about 50% ether; preferably hexane/THF (1/1). Temperature is not critical, about −100° to about 0° is operable, preferred is about −40° to about −30°. The order of addition of reactants is not critical so long as the base is added last.

The protected 21-halo steroid (IV) is then transformed to the corresponding protected 21-ester (V) by means known to those skilled in the art, see Organic Reactions in Steroid Chemistry, Vol II, Fried and Edwards, Van Nostrand editor, Reinhold Co, N.Y., 1972, p. 217–227.

The protected 21-ester (V) is transformed to the corresponding corticoid (VI) by means known to those skilled in the art.

The protection of the steroid A-ring is necessary during the transformation of the protected cyanohydrin (II) to the protected aldehyde (III) and then for the protected aldehyde (III) to the 21-halo steroid (IV). While it is not necessary, in a number of cases it is desirable to leave the $C_3$ protecting group on after the protected 21-halo steroid (IV) is obtained. When desired the protecting groups are removed by means known to those skilled in the art. Hence, the nature of the steroid nucleus does not change during the reaction. In the present invention all process chemistry changes take place in the side chain attached to $C_{17}$. Therefore, for simplicity the traditional 4 ring steroid nucleus in the present process has been defined in CHART B and identified as "STEROID".

DEFINITIONS AND CONVENTIONS

The definitions and explanations below are for the terms as used throughout this entire document including both the specification and the claims.

I. CONVENTIONS FOR FORMULAS AND DEFINITIONS OF VARIABLES

The chemical formulas representing various compounds or molecular fragments in the specification and claims may contain variable substituents in addition to expressly defined structural features. These variable substituents are identified by a letter or a letter followed by a numerical subscript, for example, "$Z_1$" or "$R_i$" where "i" is an integer. These variable substituents are either monovalent or bivalent, that is, they represent a group attached to the formula by one or two chemical bonds. For example, a group $Z_1$ would represent a bivalent variable if attached to the formula $CH_3$-$C(=Z_1)H$. Groups $R_i$ and $R_j$ would represent monovalent variable substituents if attached to the formula $CH_3$—$CH_2$—$C(R_i)(R_j)H_2$. When chemical formulas are drawn in a linear fashion, such as those above, variable substituents contained in parentheses are bonded to the atom immediately to the left of the variable substituent enclosed in parenthesis. When two or more consecutive variable substituents are enclosed in parentheses, each of the consecutive variable substituents is bonded to the immediately preceding atom to the left which is not enclosed in parentheses. Thus, in the formula above, both $R_i$ and $R_j$ are bonded to the preceding carbon atom. Also, for any molecule with an established system of carbon atom numbering, such as steroids, these carbon atoms are designated as $C_i$, where "i" is the integer corresponding to the carbon atom number. For example, $C_6$ represents the 6 position or carbon atom number in the steroid nucleus as traditionally designated by those skilled in the art of steroid chemistry. Likewise the term "$R_6$" represents a variable substituent (either monovalent or bivalent) at the $C_6$ position.

Chemical formulas or portions thereof drawn in a linear fashion represent atoms in a linear chain. The symbol "—" in general represents a bond between two atoms in the chain. Thus $CH_3$—O—$CH_2$—CH-($R_i$)—$CH_3$ represents a 2-substituted-1-methoxypropane compound. In a similar fashion, the symbol "=" represents a double bond, e.g., $CH_2$=$C(R_i)$-O-$CH_3$, and the symbol "≡" represents a triple bond, e.g., HC≡C—$CH(R_i)$—$CH_2$—$CH_3$. Carbonyl groups are represented in either one of two ways: —CO— or —C(=O)—, with the former being preferred for simplicity.

Chemical formulas of cyclic (ring) compounds or molecular fragments can be represented in a linear fashion. Thus, the compound 4-chloro-2-methylpyridine can be represented in linear fashion by $N^*$=$C(CH_3)$—CH=CCl—CH=$C^*H$ with the convention that the atoms marked with an asterisk (*) are bonded to each other resulting in the formation of a ring. Likewise, the cyclic molecular fragment, 4-(ethyl)-1-piperazinyl can be represented by —$N^*$—$(CH_2)_2$—$N(C_2H_5)$—$CH_2$-$C^*H_2$.

A cyclic (ring) structure for any compound herein defines an orientation with respect to the plane of the ring for substituents attached to each carbon atom of the cyclic compound. In formulas depicting such compounds, a substituent attached to a carbon atom below the plane of the ring is identified as being in the alpha (α) configuration and is indicated by a broken, dashed or dotted line attachment to the carbon atom, i.e., by the symbol "— — —" or "...". The corresponding substituent attached above the plane of the ring is identified as being in the beta (β) configuration.

When a variable substituent is bivalent, the valences may be taken together or separately or both in the definition of the variable. For example, a variable $R_i$ attached to a carbon atom as —C(=$R_i$)— might be bivalent and be defined as oxo or keto (thus forming a carbonyl group (—CO—) or as two separately attached monovalent variable substituents α—$R_{i-j}$ and β—$R_{i-k}$. When a bivalent variable, $R_i$, is defined to consist of two monovalent variable substituents, the convention used to define the bivalent variable is of the form "α$R_{i-j}$:β$R_{i-k}$" or some variant thereof. In such a case both α-$R_{i-j}$ and β-$R_{i-k}$ are attached to the carbon atom to yield —C(α-$R_{i-j}$)(β-$R_{i-k}$)—. For example, when the bivalent variable $R_6$, —C(=$R_6$)— is defined to consist of two monovalent variable substituents, two monovalent variable substituents are α-$R_{6-1}$:β-$R_{6-2}$, ... α-$R_{6-9}$:β-$R_{6-10}$, etc, yielding —C(α-$R_{6-1}$)(β-$R_{6-2}$)—, ... —C(α-$R_{6-9}$)(β-$R_{6-10}$)—, etc. Likewise, for the bivalent variable $R_{11}$, —C(=$R_{11}$)—, two monovalent variable substituents are α-$R_{11-1}$:β-$R_{11-2}$. For a ring substituent for which separate α and β orientations do not exist (e.g. due to the presence of a carbon carbon double bond in the ring), and for a substituent bonded to a carbon atom which is not part of a ring the above convention is still used, but the α and β designations are omitted.

Just as a bivalent variable may be defined as two separate monovalent variable substituents, two separate monovalent variable substituents may be defined to be taken together to form a bivalent variable. For example, in the formula —$C_1(R_i)H$—$C_2(R_j)H$— ($C_1$ and $C_2$ define arbitrarily a first and second carbon atom, respectively) $R_i$ and $R_j$ may be defined to be taken together to form (1) a second bond between $C_1$ and $C_2$ or (2) a bivalent group such as oxa (—O—) and the formula thereby describes an epoxide. When $R_i$ and $R_j$ are taken together to form a more complex entity, such as the group —X—Y—, then the orientation of the entity is such that $C_1$ in the above formula is bonded to X and $C_2$ is bonded to Y. Thus, by convention the designation "... $R_i$ and $R_j$ are taken together to form —$CH_2$—$CH_2$—O—CO—..." means a lactone in which the carbonyl is bonded to $C_2$. However, when designated "... $R_j$ and $R_i$ are taken together to form —$CH_2$—$CH_2$—O—CO— the convention means a lactone in which the carbonyl is bonded to $C_1$.

The carbon atom content of variable substituents is indicated in one of two ways. The first method uses a prefix to the entire name of the variable such as "$C_1$-$C_4$", where both "1" and "4" are integers representing the minimum and maximum number of carbon atoms in the variable. The prefix is separated from the variable by a space. For example, "$C_1$-$C_4$ alkyl" represents alkyl of 1 through 4 carbon atoms, (including isomeric forms thereof unless an express indication to the contrary is given). Whenever this single prefix is given, the prefix indicates the entire carbon atom content of the variable being defined. Thus $C_2$-$C_4$ alkoxycarbonyl describes a group $CH_3$—$(CH_2)_n$—O—CO— where n is zero, one or 2. By the second method the carbon atom content of only each portion of the definition is indicated separately by enclosing the "Ci—Cj" designation in parentheses and placing it immediately (no intervening space) before the portion of the definition being defined. By this optional convention ($C_1$-$C_3$)alkoxycarbonyl has the same meaning as $C_2$-$C_4$ alkoxycarbonyl because the "$C_1$-$C_3$" refers only to the carbon atom content of the alkoxy group. Similarly while both $C_2$-$C_6$ alkoxyalkyl and ($C_1$-Chd 3)alkoxy($C_1$-$C_3$)alkyl define alkoxyalkyl groups containing from 2 to 6 carbon atoms, the two definitions differ since the former definition allows either the alkoxy or alkyl portion alone to contain 4 or 5 carbon atoms while the latter definition limits either of these groups to 3 carbon atoms.

When the claims contain a fairly complex (cyclic) substituent, at the end of the phrase naming/designating that particular substituent will be a notation in (parentheses) which will correspond to the same name/designation in one of the CHARTS which will also set forth the chemical structural formula of that particular substituent.

II. DEFINITIONS

STEROID refers to the steroid nucleus as set forth in CHARTS A, B and C.

All temperatures are in degrees Centigrade.

TLC refers to thin-layer chromatography.

HPLC refers to high pressure liquid chromatography.

THF refers to tetrahydrofuran.

LDA refers to lithium diisopropylamide.

Saline refers to an aqueous saturated sodium chloride solution.

NMR refers to nuclear (proton) magnetic resonance spectroscopy, chemical shifts are reported in ppm ($\delta$) downfield from tetramethylsilane.

$\phi$ refers to phenyl ($C_6H_5$).

Ether refers to diethyl ether.

When solvent pairs are used, the ratios of solvents used are volume/volume (v/v).

Androstenedione refers to androst-4-ene-3,17-dione.

EXAMPLES

Without further elaboration, it is believed that one skilled in the art can, using the preceding description, practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

EXAMPLE 1

3,17α-Dihydroxyandrosta-3,5,9(11)-triene-17β-carboxaldehyde 3-methyl 17-trimethylsilyloxy diether (III)

17β-Cyano-3,17α-dihydroxyandrosta -3,5,9(11)-triene 3-methyl 17-trimethylsilyloxy diether (II, 17.46 g) is dissolved in methyl t-butyl ether (50 ml) and THF (5.7 ml). The resulting solution is cooled to −28°. Diisobutylaluminum hydride (12.6 ml) is dissolved in methyl t-butyl ether (26.6 ml) and this solution is cooled to −30° before being added dropwise to the steroid mixture. The addition is done over 35 min and the reaction temperature is maintained between −25° and −30°. Following the addition, the mixture is allowed to warm to 0° slowly over 2.5 hr at which time the reaction is complete as measured by TLC.

Methanol (5.5 ml) is added dropwise while maintaining the temperature between 0° and 10°. After stirring, the resulting cloudy mixture for 10 min a solution of aqueous acetic acid (50%, 66 ml) is slowly added while maintaining the temperature below 25°. After stirring the resulting two-phase mixture at 25° for 0.5 hr, toluene (70 ml) is added and the mixture is distilled under vacuum at 30° until 50 ml of distillate are collected. The two phases are separated and the aqueous fraction is extracted with toluene (2-15 ml). The combined organic phases are washed twice with water (20 ml), then with saturated sodium bicarbonate (20 ml), then with water again (20 ml), and then finally with saline (20 ml). After drying over anhydrous magnesium sulfate (1 g) and silica gel (5 g), the mixture is filtered and the solvent is removed under reduced pressure to give an oily residue. TLC and HPLC indicate that the product is >95% pure.

The product is crystallized by dissolving it in a minimum of ethyl acetate and adding methanol until it becomes cloudy. After gentle heating and then cooling to 25° seed crystals are added and the mixture is then left at −15° for 15 hr. Filtration gives a solid which is crystallized to give the title compound, mp=90°-92°.

A second crop can be obtained following silica gel chromatography of the mother liquor eluting with hexane/acetone (98/2), NMR ($CDCl_3$) 0.1, 0.65, 1.15, 3.6, 5.2, 5.3, 5.5 and 9.65 $\delta$.

EXAMPLE 2

21-Bromo-17α-hydroxypregna-4,9(11)-diene-3,20-dione 17-trimethylsilyloxy ether (IV)

3,17α-Dihydroxyandrosta-3,5,9(11)-triene-17β-carboxaldehyde 3-methyl 17-trimethylsilyloxy diether (III, EXAMPLE 1, 1.18 g) is dissolved in THF (1.2 ml) and hexane (2.3 ml) is added. After degassing with nitrogen, the solution is cooled to −35° and methylene bromide (0.22 ml) is added. A solution of lithium diisopropylamide in THF/hexane (1M, ~2:1) is then added dropwise over 10 min maintaining the temperature between −30° and −35°. The resulting mixture is then stirred for ½ hr during which time the temperature is allowed to climb to −10°. The mixture is then transferred to a flask containing hydrochloric acid (3N, 7 ml) and methylene chloride (3 ml) which is previously cooled to −20°. A 10° exotherm is observed during this addition. The resulting mixture is then allowed to warm up to 20°–25°. After a total hydrolysis time of 1.5 hr methylene chloride (30 ml) is added and the two layers are separated. The aqueous phase is extracted with methylene chloride (5 ml) and the combined organic fractions are washed successively with water (10 ml), sodium bicarbonate (10% 10 ml) and saline (10 ml). After drying over anhydrous magnesium sulfate (~1 g) and filtering through a short column of silica gel (~5 g, eluting with about 10 ml methylene chloride), the solvent is removed to give the title compound, mp=155°–156°; NMR (CDCl$_3$) 0.15, 0.55, 1.35, 4.1, 4.3, 5.6 and 5.75 δ.

EXAMPLE 3

3,3,17α-Trihydroxyandrost-5-ene-17β-carboxaldehyde 3,3-ethylene ketal 17-trimethylsilyloxy ether (III)

Following the general procedure of EXAMPLE 1 and making noncritical variations but starting with 17β-cyano-3,3,17α-trihydroxyandrost-5-ene 3,3-ethylene ketal 17-trimethylsilyloxy ether (II) the title compound is obtained, mp=128°–134°.

EXAMPLE 4

21-Bromo-17α-hydroxypregn-4-ene-3,20-dione 17-tri methylsilyloxy ether (IV)

Following the general procedure of EXAMPLE 2 and making noncritical variations but starting with 3,3,17α-trihydroxyandrost-5-ene-17β-carboxaldehyde 3,3-ethylene ketal 17-trimethylsilyloxy ether (III, EXAMPLE 3) the title compound is obtained, NMR (CDCl$_3$) 0.15, 0.6, 1.15, 4.1, 4.3 and 5.75 δ; TLC (methylene chloride/methanol, 98/2) R$_f$=0.64; TLC (methylene chloride/acetone, 95/5) R$_f$=0.68.

EXAMPLE 5

3,3,17α-Trihydroxyandrosta-5,9(11)-diene-17β-carboxaldehyde 3,3-ethylene ketal 17-trimethylsilyloxy ether (III)

Following the general procedure of EXAMPLE 1 and making noncritical variations but starting with 17β-cyano-3,3,17α-trihydroxyandrosta-5,9(11)-diene 3,3-ethylene ketal 17-trimethylsilyloxy ether (II) the title compound is obtained mp=131°–134°.

EXAMPLE 6

21-Bromo-17α-hydroxypregna-4,9(11)-diene-3,20-dione 17-trimethylsilyloxy ether (IV)

Following the general procedure of EXAMPLE 2 and making noncritical variations but starting with 3,3,17α-trihydroxyandrosta-5,9(11)-diene-17β-carboxaldehyde 3,3-ethylene ketal 17-trimethylsilyloxy ether (III, EXAMPLE 5) the title compound is obtained.

CHART A

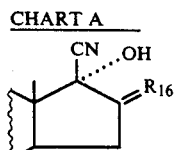
(I)

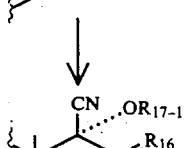
(II)

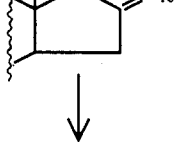
(III)

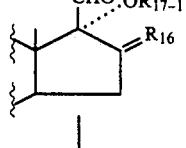
(IV)

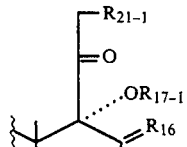
(V)

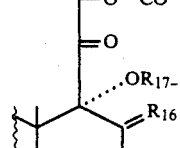
(VI)

CHART B

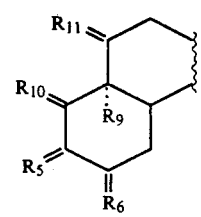
(A/B/C)

where:

(A-I) $R_5$ is $R_{5-1}$:$R_{5-2}$, $R_6$ is $R_{6-1}$:$R_{6-2}$, $R_{10}$ is $\alpha$-$R_{10-1}$:$\beta$-$R_{10-2}$ where one of $R_{6-1}$ and $R_{6-2}$ is —H, —F, —Cl, —Br, —CH$_3$ and the other taken together with one of $R_{5-1}$ and $R_{5-2}$ forms a second bond between $C_5$ and $C_6$, $R_{10-2}$ is —CH$_3$, $R_{10-1}$ and the other of $R_{5-1}$ and $R_{5-2}$ taken together are —CH$_2$—CH$_2$—C($R_{3-1}$)=CH— or —CH=CH—C($R_{3-1}$)=CH— where $R_{3-1}$ is $C_1$-$C_6$ alkyloxy, —O—$\phi$ where $\phi$ is optionally substituted with 1 $C_1$-$C_4$ alkyl or —N($R_{3-2}$)($R_{3-6}$) where $R_{3-2}$ is $C_1$-$C_3$ alkyl, $R_{3-6}$ is $C_{1-3}$ alkyl or $\phi$, where the $R_{3-2}$ and $R_{3-6}$ may be cyclized to form a heterocyclic ring selected from the group consisting of pyrollidine, piperidine, morpholine, piperazine;

(A-II) $R_5$ is $R_{5-3}$:$R_{5-4}$, $R_6$ is $R_{6-3}$:$R_{6-4}$, $R_{10}$ is $\alpha$-$R_{10-3}$:$\beta$-$R_{10-4}$, where one of $R_{6-3}$ and $R_{6-4}$ is —H, —F, —Cl, —Br, —CH$_3$ and the other taken together with one of $R_{5-3}$ and $R_{5-4}$ forms a second bond between $C_5$ and $C_6$, $R_{10-4}$ is —CH$_3$, $R_{10-3}$ and the other of $R_{5-3}$ and $R_{5-4}$ taken together are —CH$_2$—CH$_2$—C($\alpha$-$R_{3-3}$)($\beta$-$R_{3-4}$)—CH$_2$—, where one of $R_{3-3}$ and $R_{3-4}$ is —H and the other of $R_{3-3}$ and $R_{3-4}$ is —OH or —OR$_{3-5}$ where $R_{3-5}$ is $C_1$-$C_6$ alkyl, —CH$_2$-$\phi$ or —Si—($R_{3-7}$)$_2$($R_{3-8}$) where $R_{3-7}$ and $R_{3-8}$ are $C_{1-4}$ and $\phi$, and where $R_{3-3}$ and $R_{3-4}$ taken together are —O—CH$_2$C(CH$_3$)$_2$—CH$_2$—O— or —O—(CH$_2$)$_{n1}$—O— where $n_1$ is 2 or 3;

(C-I) $R_{11}$ is $R_{11-1}$:$R_{11-2}$ where one of $R_{11-1}$ and $R_{11-2}$ taken together with $R_9$ to form a second bond between $C_9$ and $C_{11}$ and the other of $R_{11-1}$ and $R_{11-2}$ is —H;

(C-II) $R_{11}$ is $\alpha$-H:$\beta$—O—, where $\beta$—O— is taken together with $R_9$ to form a $\beta$-epoxide between $C_9$ and $C_{11}$;

CHART B -Continued (C-III) $R_9$ is —H and $R_{11}$ is —O—CH$_2$—C(CH$_3$)$_2$—O— or —O—(—CH$_2$)$_{n2}$—O— where $n_2$ is 2 or 3, $\alpha$-$R_{11-3}$:$\beta$-$R_{11-4}$ where one of $R_{11-3}$ and $R_{11-4}$ is —H and the other of $R_{11-3}$ and $R_{11-4}$ is —H, —OH or —OR$_{11-5}$ where $R_{11-5}$ is $C_1$-$C_6$ alkyl, —CH$_2$-$\phi$ or —Si—($R_{11-6}$)$_2$($R_{11-7}$) where $R_{11-6}$ and $R_{11-7}$ are $C_{1-4}$ and $\phi$.

CHART C

The six partial structural formulas of CHART A can be represented by

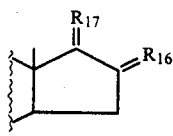 (VII)

where $R_{16}$ is $\alpha$-$R_{16-1}$:$\beta$-$R_{16-2}$ where one of $R_{16-1}$ and $R_{16-2}$ is —H and the other of $R_{16-1}$ and $R_{16-2}$ is —H, —CH$_3$ or —OH;

where for the cyanohydrin (I) $R_{17}$ is $\alpha$—OH: $\beta$-CN, for the protected cyanohydrin (II) $R_{17}$ is $\alpha$-OR$_{17-1}$:$\beta$-CN, for the protected aldehyde (III) $R_{17}$ is $\alpha$-OR$_{17-1}$:$\beta$-CHO, for the protected 21-halo steroid (IV) $R_{17}$ is $\alpha$-OR$_{17-1}$:$\beta$-CO—CH$_2$-$R_{21-1}$, for the protected 21-ester (V) $R_{17}$ is $\alpha$-OR$_{17-1}$:$\beta$-CO—CH$_2$—O—CO—$R_{21-2}$ and for the corticoid (VI) $R_{17}$ is $\alpha$—OH:$\beta$—CO—CH$_2$—O—CO—$R_{21-2}$.

CHART D

STEROID-17$\alpha$[—OH]—17$\beta$[—CN]    (I)

-continued
CHART D

↓

STEROID-17$\alpha$[—OR$_{17-1}$]—17$\beta$[—CN]    (II)

↓

STEROID-17$\alpha$[—OR$_{17-1}$]—17$\beta$[—CHO]    (III)

↓

STEROID-17$\alpha$[—OR$_{17-1}$]—17$\beta$[—CO—CH$_2$—$R_{21-1}$]    (IV)

↓

STEROID-17$\alpha$[—OR$_{17-1}$]—17$\beta$[—OC—CH$_2$—O—CO—$R_{21-2}$]    (V)

↓

STEROID-17$\alpha$[—OH]—17$\beta$[—CO—CH$_2$—O—CO—$R_{21-2}$]    (VI)

STEROID refers to the steroid nucleus as set forth in CHARTS A, B and C.

We claim:

1. A protected aldehyde of formula III-A/B/C

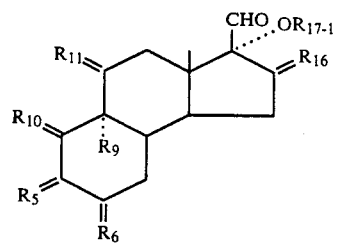 (III-A/B/C)

where (A-I) $R_5$ is $R_{5-1}$:$R_{5-2}$, $R_6$ is $R_{6-1}$:$R_{6-2}$, $R_{10}$ is $\alpha$-$R_{10-1}$:$\beta$-$R_{10-2}$ where one of $R_{6-1}$ and $R_{6-2}$ is —H, —F, —Cl, —Br, —CH$_3$ and the other taken together with one of $R_{5-1}$ and $R_{5-2}$ forms a second bond between $C_5$ and $C_6$, $R_{10-2}$ is —CH$_3$, $R_{10-1}$ and the other of $R_{5-1}$ and $R_{5-2}$ taken together are —CH$_2$—CH$_2$—C($R_{3-1}$)=CH— or —CH=CH—C($R_{3-1}$)=CH— where $R_{3-1}$ is $C_1$-$C_6$ alkyloxy, —O—$\phi$ where $\phi$ is optionally substituted with 1 $C_1$-$C_4$ alkyl or —N($R_{3-2}$)($R_{3-6}$) where $R_{3-2}$ is $C_1$-$C_3$ alkyl, $R_{3-6}$ is $C_{1-3}$ alkyl or $\phi$, where the $R_{3-2}$ and $R_{3-6}$ may be cyclized to form a heterocyclic ring selected from the group consisting of pyrollidine, piperidine, morpholine, piperazine;

(A-II) $R_5$ is $R_{5-3}$:$R_{5-4}$, $R_6$ is $R_{6-3}$:$R_{6-4}$, $R_{10}$ is $\alpha$-$R_{10-3}$:$\beta$-$R_{10-4}$, where one of $R_{6-3}$ and $R_{6-4}$ is —H, —F, —Cl, —Br, —CH$_3$ and the other taken together with one of $R_{5-3}$ and $R_{5-4}$ forms a second bond between $C_5$ and $C_6$, $R_{10-4}$ is —CH$_3$, $R_{10-3}$ and the other of $R_{5-3}$ and $R_{5-4}$ taken together are —CH$_2$—CH$_2$—C($\alpha$-$R_{3-3}$)($\beta$-$R_{3-4}$)—CH$_2$—, where one of $R_{3-3}$ and $R_{3-4}$ is —H and the other of $R_{3-3}$ and $R_{3-4}$ is —OH or —OR$_{3-5}$ where $R_{3-5}$ is $C_1$-$C_6$ alkyl, —CH$_2$-$\phi$ or —Si—($R_{3-7}$)$_2$($R_{3-8}$) where $R_{3-7}$ and $R_{3-8}$ are $C_{1-4}$ and $\phi$, and where $R_{3-3}$ and $R_{3-4}$ taken together are —O—CH$_2$C(CH$_3$)$_2$CH$_2$—O— or —O—(CH$_2$)$_{n1}$—O— where $n_1$ is 2 or 3;

13

(C-I) $R_{11}$ is $R_{11-1}$:$R_{11-2}$ where one of $R_{11-1}$ and $R_{11-2}$ taken together with $R_9$ to form a second bond between $C_9$ and $C_{11}$ and the other of $R_{11-1}$ and $R_{11-2}$ is —H;

(C-II) $R_{11}$ is $\alpha$-H:$\beta$—O—, where $\alpha$—O— is taken together with $R_9$ to form a $\beta$-epoxide between $C_9$ and $C_{11}$;

(C-III) $R_9$ is —H and $R_{11}$ is —O—CH$_2$—C(CH$_3$)$_2$—CH$_2$—O— or —O—(CH$_2$)$_{n2}$—O— O— where $n_2$ is 2 or 3, $\alpha$-$R_{11-3}$:$\beta$-$R_{11-4}$ where one of $R_{11-3}$ and $R_{11-4}$ is —H and the other of $R_{11-3}$ and $R_{11-4}$ is —H, —OH or —OR$_{11-5}$ where $R_{11-5}$ is $C_1$-$C_6$ alkyl, —CH$_2$—$\phi$ or —Si—($R_{11-6}$)$_2$($R_{11-7}$) where $R_{11-6}$ and $R_{11-7}$ are $C_{1-4}$ and $\phi$;

$R_{16}$ is $\alpha$-$R_{16-1}$:$\beta$-$R_{16-2}$ where one of $R_{16-1}$ and $R_{16-2}$ is —H and the other of $R_{16-1}$ and $R_{16-2}$ is —H, —CH$_3$ or —OH;

$R_{17-1}$ is —Si—($R_{17-2}$)$_2$($R_{17-3}$) where $R_{17-2}$ and $R_{17-3}$ are $C_1$-$C_4$ alkyl or $\phi$.

2. A protected aldehyde (III) according to claim 1 where $R_{17-1}$ is trimethylsilyl.

3. A protected aldehyde (III) according to claim 1 where (A-I) $R_5$ is $R_{5-1}$:$R_{5-2}$, $R_6$ is $R_{6-1}$:$R_{6-2}$, $R_{10}$ is $\alpha$-$R_{10-1}$:$\beta$-$R_{10-2}$ where one of $R_{6-1}$ and $R_{6-2}$ is —H and the other taken together with one of $R_{5-1}$ and $R_{5-2}$ forms a second bond between $C_5$ and $C_6$, $R_{10-2}$ is —CH$_3$, $R_{10-1}$ and the other of $R_{5-1}$ and $R_{5-2}$ taken together are —CH$_2$CH$_2$—C($R_{3-1}$)=CH— where $R_{3-1}$ is $C_1$-$C_6$ alkyloxy, —O—$\phi$ where $\phi$ is optionally substituted with 1 $C_1$-$C_4$ alkyl;

(A-II) $R_5$ is $R_{5-3}$:$R_{5-4}$, $R_6$ is $R_{6-3}$:$R_{6-4}$ and $R_{10}$ is $\alpha$-$R_{10-3}$:$\beta$-$R_{10-4}$, where one of $R_{6-3}$ and $R_{6-4}$ is —H, and the other taken together with one of $R_{5-3}$ and $R_{5-4}$ forms a second bond between $C_5$ and $C_6$, $R_{10-4}$ is —CH$_3$, $R_{10-3}$ and the other of $R_{5-3}$ and $R_{5-4}$ taken together are —CH$_2$—CH$_2$—C($\alpha$-$R_{3-3}$)($\beta$-$R_{3-4}$)—CH$_2$—, where $R_{3-3}$ and $R_{3-4}$ taken together are —O—CH$_2$—C(CH$_3$)$_2$—CH$_2$—O— or —O—(CH$_2$)$_{n1}$—O— where $n_1$ is 2 or 3.

4. A protected aldehyde (III) according to claim 1 where $R_{11}$ is $R_{11-1}$:$R_{11-2}$ or $\alpha$-$R_{11-3}$:$\beta$-$R_{11-3}$ where $R_{11-3}$ and $R_{11-4}$ are both —H.

5. A protected aldehyde (III) according to claim 1 where $R_{16-1}$ and $R_{16-2}$ are both —H.

6. A protected aldehyde (III) according to claim 1 which is selected from the group consisting of
3,17$\alpha$-dihydroxyandrosta-3,5,9(11)-triene-17$\beta$-carboxaldehyde 3-methyl 17-trimethylsilyloxy diether,
3,3,17$\alpha$-trihydroxyandrost-5-ene-17$\beta$-carboxaldehyde 3,3-ethylene ketal 17-trimethylsilyloxy ether,
3,3,17$\alpha$-trihydroxyandrosta-5,9(11)-diene-17$\beta$-carboxaldehyde 3,3-ethylene ketal 17-trimethylsilyloxy ether.

7. A process for the preparation of a protected 21-halo steroid of formula (IV) where
$R_{16}$ is $\alpha$-$R_{16-1}$:$\beta$-$R_{16-2}$ where one of $R_{16-1}$ and $R_{16-2}$ is —H and the other of $R_{16-1}$ and $R_{16-2}$ is —H, —CH$_3$ or —OH;
$R_{17-1}$ is —Si—($R_{17-2}$)$_2$($R_{17-3}$) where $R_{17-2}$ and $R_{17-3}$ are $C_1$-$C_4$ alkyl or $\phi$;
$R_{21-1}$ is —Cl or —Br which comprises
(1) contacting a protected cyanohydrin of formula (II)
where $R_{16}$ and $R_{17-1}$ are as defined above with at least one hydride equivalent of a reducing agent in the presence of an ether and

14

(2) hydrolyzing the reaction mixture of step (1) to produce a protected aldehyde of formula (III)

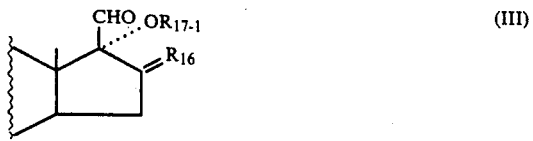

where $R_{16}$ and $R_{17-1}$ are as defined above and
(3) contacting the protected aldehyde of formula (II) with a strong base in the presence of a compound of the formula CH$_2$($R_{21-1}$)$_2$ where $R_{21-1}$ is as defined above.

8. A process according to claim 7 for the preparation of a protected 21-halo steroid of formula (IV) where the reducing agent is an aluminum hydride.

9. A process according to claim 7 for the preparation of a protected 21-halo steroid of formula (IV) where about 1.2 to about 2.0 equivalents of reducing agent are used.

10. A process according to claim 7 for the preparation of a protected 21-halo steroid of formula (IV) where the ether is selected from the group consisting of THF, ether and methyl t-butyl ether and mixtures thereof.

11. A process according to claim 7 for the preparation of a protected 21-halo steroid of formula (IV) where the hydrolysis is performed with aqueous acid.

12. A process according to claim 7 for the preparation of a protected 21-halo steroid of formula (IV) where the strong base is selected from the group consisting of amides of the formula Metal-N-($R_1$)$_2$ where Metal is lithium, sodium, potassium and magnesium and $R_1$ is —H, $C_1$-$C_6$ alkyl, —Si($R_2$)$_3$ where $R_2$ is $C_1$-$C_6$ alkyl.

13. A process according to claim 7 for the preparation of a protected 21-halo steroid of formula (IV) where <3 equivalents of the strong base are used.

14. A process according to claim 7 for the preparation of a protected 21-halo steroid of formula (IV) where the steroid A-B-C rings are

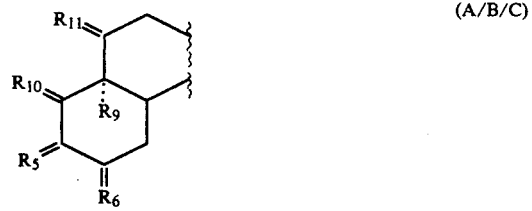

(A/B/C)

where:
(A-I) $R_5$ is $R_{5-1}$:$R_{5-2}$, $R_6$ is $R_{6-1}$:$R_{6-2}$, $R_{10}$ is $\alpha$-$R_{10-1}$:$\beta$-$R_{10-2}$ where one of $R_{6-1}$ and $R_{6-2}$ is —H, —F, —Cl, —Br, —CH$_3$ and the other taken together with one of $R_{5-1}$ and $R_{5-2}$ forms a second bond between $C_5$ and $C_6$, $R_{10-2}$ is —CH$_3$, $R_{10-1}$ and the other of $R_{5-1}$ and $R_{5-2}$ taken together are —CH$_2$—CH$_2$—C($R_{3-1}$)=CH— or —CH=CH—C($R_{3-1}$)=CH— where $R_{3-1}$ is $C_1$-$C_6$ alkyloxy, —O—$\phi$ where $\phi$ is optionally substituted with 1 $C_1$-$C_4$ alkyl or —N($R_{3-2}$)($R_{3-6}$) where $R_{3-2}$ is $C_1$-$C_3$ alkyl, $R_{3-6}$ is $C_{1-3}$ alkyl or $\phi$, where the $R_{3-2}$ and $R_{3-6}$ may be cyclized to form a heterocyclic ring selected from the group consisting of pyrollidine, piperidine, morpholine, piperazine;

(A-II) $R_5$ is $R_{5-3}$:$R_{5-4}$, $R_6$ is $R_{6-3}$:$R_{6-4}$, $R_{10}$ is $\alpha$-$R_{10-3}$:$\beta$-$R_{10-4}$, where one of $R_{6-3}$ and $R_{6-4}$ is —H, —F, —Cl, —Br, —CH$_3$ and the other taken together with one of $R_{5-3}$ and $R_{5-4}$ forms a second bond between C$_5$ and C$_6$, $R_{10-4}$ is —CH$_3$, $R_{10-3}$ and the other of $R_{5-3}$ and $R_{5-4}$ taken together are —CH$_2$—CH$_2$—C($\alpha$-$R_{3-3}$)($\beta$-$R_{3-4}$)—CH$_2$—, where one of $R_{3-3}$ and $R_{3-4}$ is —H and the other of $R_{3-3}$ and $R_{3-4}$ is —OH or —OR$_{3-5}$ where $R_{3-5}$ is C$_1$-C$_6$ alkyl, —CH$_2$—$\phi$ or —Si—(R$_{3-7}$)$_2$(R$_{3-8}$) where $R_{3-7}$ and $R_{3-8}$ are C$_{1-4}$ and $\phi$, and where $R_{3-3}$ and $R_{3-4}$ taken together are —O—CH$_2$C(CH$_3$)$_2$CH$_2$—O— or —O—(CH$_2$)$_{n_1}$—O— where $n_1$ is 2 or 3;

(C-I) $R_{11}$ is $R_{11-1}$:$R_{11-2}$ where one of $R_{11-1}$ and $R_{11-2}$ taken together with $R_9$ to form a second bond between C$_9$ and C$_{11}$ and the other of $R_{11-1}$ and $R_{11-2}$ is —H;

(C-II) $R_{11}$ is $\alpha$-H:$\beta$-O—, where $\alpha$—O— is taken together with $R_9$ to form a $\beta$-epoxide between C$_9$ and C$_{11}$;

(C-III) $R_9$ is —H and $R_{11}$ is —O—CH$_2$—C(CH$_3$)$_2$—CH$_2$—O— or —O—(CH$_2$)$_{n_2}$—O— where $n_2$ is 2 or 3, $\alpha$-$R_{11-3}$:$\beta$-$R_{11-4}$ where one of $R_{11-3}$ and $R_{11-4}$ is —H and the other of $R_{11-3}$ and $R_{11-4}$ is —H, —OH or —OR$_{11-5}$ where $R_{11-5}$ is C$_1$-C$_6$ alkyl, —CH$_2$—$\phi$ or —Si—(R$_{11-6}$)$_2$(R$_{11-7}$) where $R_{11-6}$ and $R_{11-7}$ are C$_{1-4}$ and $\phi$.

15. A process according to claim 7 for the preparation of a protected 21-halo steroid of formula (IV) which is selected from the group consisting of 3,17$\alpha$-dihydroxyandrosta-3,5,9(11)-triene-17$\beta$-carboxaldehyde 3-methyl 17-trimethylsilyloxy diether, 3,3,17$\alpha$-trihydroxyandrost-5-ene-17$\beta$-carboxaldehyde 3,3-ethylene ketal 17-trimethylsilyloxy ether, 3,3,17$\alpha$-trihydroxyandrosta-5,9(11)-diene-17$\beta$-carboxaldehyde 3,3-ethylene ketal 17-trimethylsilyloxy ether.

16. A process for the preparation of a protected 21-halo steroid according to claim 11 where 1.00–1.05 equivalents of CH$_2$(R$_{21-1}$)$_2$ are used.

* * * * *